(12) United States Patent
Wenger et al.

(10) Patent No.: US 8,044,246 B2
(45) Date of Patent: Oct. 25, 2011

(54) PROCESS FOR THE SELECTIVE PREPARATION OF ACETALDEHYDE FROM ACROLEIN AND ONE OR MORE AMMONIUM SALTS DISSOLVED IN WATER

(75) Inventors: Wolfgang Wenger, Visp (CH); Andreas Heyl, Termen (CH); Lothar Ott, Visp (CH); Herbert Vogel, Nauheim (DE); Paul Hanselmann, Brig-Glis (CH); Gökhan Aras, Babenhausen (DE)

(73) Assignee: Lonza Ltd., Basel (CH)

( * ) Notice: Subject to any disclaimer, the term of this patent is extended or adjusted under 35 U.S.C. 154(b) by 0 days.

(21) Appl. No.: 12/844,571

(22) Filed: Jul. 27, 2010

(65) Prior Publication Data

US 2011/0028764 A1 Feb. 3, 2011

Related U.S. Application Data

(60) Provisional application No. 61/229,599, filed on Jul. 29, 2009.

(30) Foreign Application Priority Data

Jul. 29, 2009 (EP) .................................... 09009822

(51) Int. Cl.
*C07C 45/61* (2006.01)
(52) U.S. Cl. ........................ 568/458; 568/465
(58) Field of Classification Search .................. 568/458, 568/465
See application file for complete search history.

(56) References Cited

OTHER PUBLICATIONS

Antal Jr. et al., "Pyrolytic Sources of Hydrocarbons from Biomass", Journal of Analytical and Applied Pyrolysis, vol. 8, pp. 291-303; 1985.
Antal Jr. et al., "Catalyzed and Uncatalyzed Conversion of Cellulose Biopolymer Model Compounds to Chemical Feedstocks in Supercritical Solvents", Energy from Biomass and Wastes, vol. 10, pp. 865-877; 1987.
Buhler et al., "Ionic Reactions and Pyrolysis of Glycerol as Competing Reaction Pathways in Near and Supercritical Water", Journal of Supercritical Fluids, vol. 22, pp. 37-53; 2002.
Eckert et al., "Acetaldehyde", Ullmann's Encyclopedia of Industrial Chemistry, 7. Aufl., Wiley Interscience, Online Release, 2009.
Ott et al., "Catalytic Dehydration of Glycerol in Sub and Supercritical Water: A New Chemical Process for Acrolein Production", Green Chemistry, vol. 8, pp. 214-220; 2006.
Ott, Stoffliche Nutzung von Biomasse mit Hilfe von nah- und uberkritischem Wasser-homogenkatalysierte Dehydratisierung von Polyolen zu Aldehyden-[Material use of biomass with the aid of near-critical and supercritical water-homogeneously catalysed dehydration of polyols to give aldehydes], Thesis, TU Darmstadt, 2005.
Ramayya et al., Acid-Catalyzed Dehydration of Alcohols in Supercritical Water, Fuel, vol. 66, No. 10, pp. 1364-1371; 1987.
Watanabe et al., Acrolein Synthesis from Glycerol in Hot-Compressed Water, Bioresource Technology, vol. 98, pp. 1285-1290; 2007.

*Primary Examiner* — Sikarl Witherspoon
(74) *Attorney, Agent, or Firm* — Hoffmann & Baron, LLP

(57) ABSTRACT

The present invention relates to a process for the selective preparation of acetaldehyde, characterized in that acrolein and one or more ammonium salts dissolved in water are reacted continuously under high pressures and at temperatures of 300-400° C.

10 Claims, 2 Drawing Sheets

PROCESS FOR THE SELECTIVE PREPARATION OF ACETALDEHYDE FROM ACROLEIN AND ONE OR MORE AMMONIUM SALTS DISSOLVED IN WATER

This application is based on, and Applicant claims priority from, U.S. Provisional Application bearing Ser. No. 61/229,599 filed Jul. 29, 2009, and European Patent Application bearing Ser. No. EP 09009822.9 filed Jul. 29, 2009, both of which are incorporated herein by reference.

BACKGROUND OF THE INVENTION

The present invention relates to a process for the selective and continuous preparation of acetaldehyde from acrolein.

A considerable proportion of acetaldehyde is used for the preparation of acetic esters. For example, ethyl acetate is prepared in a rearrangement reaction with aluminium alcoholates as a catalyst (Claisen-Tiščenko reaction). A substantial proportion is also used with formaldehyde for the production of pentaerythritol, an intermediate in the production of alkyl resins and plasticizers and emulsifiers. Furthermore, acetaldehyde is an intermediate in the preparation of butadiene starting from acetylene via acetaldol and its hydration product 1,3-butanediol. The formation of the acetaldol, which can be dehydrated to give crotonaldehyde, takes place by aldol addition of acetaldehyde. The reaction of acetaldehyde with nitrogen compounds to give pyridine and derivatives thereof is becoming increasingly important. Thus, 5-ethyl-2-methylpyridine is prepared in a liquid-phase reaction from acetaldehyde and ammonia. Addition of formaldehyde or acrolein leads to the formation of pyridine and alkylpyridines. Acetaldehyde is further used in the production of peracetic acid, in the oxidation with nitric acid to give glyoxal or glyoxalic acid and in the addition reactions with hydrocyanic acid to give lactonitrile, a precursor of acrylonitrile, and acetic anhydride to give ethylidene diacetate, an intermediate in the vinyl acetate process [Eck2007].

According to the prior art, acrolein can be prepared, inter alia, from the dehydration of glycerol, which occurs as the "waste product" in relatively large amounts in biodiesel production, in near-critical and supercritical water of the addition of acids [Wat2007] or salts [Ott2006]. In the reaction of the resulting acrolein with ammonium salts, acetaldehyde is obtained in high yields.

It is known that acetaldehyde is obtained with a yield of 26% in the dehydration of glycerol in supercritical water at 500° C. and 34.5 MPa and with a residence time of 90 s [Ant1985]. A free radical mechanism by dehydration of the glycerol to 3-hydroxy-propionaldehyde and homolytic cleavage of this intermediate to give acetaldehyde and formaldehyde is assumed for the stated conditions. An alternative mechanism via homolytic cleavage of acetol can be ruled out. The selectivity with respect to acetaldehyde is lower under near-critical water conditions at 360° C. and the same conditions. Addition of sodium hydrogen sulphate as acidic catalyst merely leads to an increase in the yield of acrolein, which presumably results from the acid-catalysed dehydration of 3-hydroxypropionaldehyde.

It is furthermore known that acetaldehyde forms as a by-product with the dehydration of glycerol in near-critical water at between 300 and 350° C. and 34.5 MPa by addition of 0.005 M sulphuric acid [Ant1987]. The reaction of a 0.5 M glycerol solution at 325° C. and with a residence time of 39 s leads to a molar yield of acetaldehyde of only 5%. A retro-aldol reaction starting from acrolein via 3-hydroxypropionaldehyde is assumed as a reaction mechanism, formaldehyde additionally forming and decomposing into hydrogen, carbon monoxide and carbon dioxide under the stated conditions. This assumption was confirmed by the use of an equimolar amount of acetaldehyde and formaldehyde and the cross-aldol reaction to give acrolein. The reaction of a dilute acetaldehyde solution under non-catalytic or alkaline conditions leads mainly to the formation of crotonaldehyde. Furthermore, acetaldehyde can be obtained as the main product by acid-catalysed dehydration from ethylene glycol. The dehydration of a 0.5 M ethylene glycol solution at 385° C. and 34.5 MPa and with a residence time of 29 s leads to a molar acetaldehyde yield of 40%. A disadvantage is the corrosive property of the sulphuric acid, especially in near-critical water.

Further investigations into the dehydration of polyols under supercritical water conditions (385° C., 34 MPa, 20-45 s residence time) are also known [Ram1987]. The acid-catalysed reaction of a 0.5 M ethylene glycol solution leads to a maximum acetaldehyde yield of 41% with 45 s residence time. Hydrogen, carbon monoxide, carbon dioxide and ethylene can be identified as by-products in small amounts. In the dehydration of glycerol in the near-critical range, acetaldehyde is obtained with a maximum yield of 12% at 350° C. and with a residence time of 25 s and addition of catalytic amounts of sulphuric acid. The back-reaction or cross-aldol reaction of acetaldehyde with formaldehyde to give acrolein leads to an acrolein yield of 22%, based on formaldehyde. Crotonaldehyde, which is formed by aldol reaction of acetaldehyde, is detected as a further liquid product. The aldol reaction can be slowed down by addition of acids.

The results of the reaction of glycerol without addition in the near-critical and supercritical water in a temperature range of 250-475° C., at pressures of 25, 35 or 45 MPa and with residence times of 32-165 s and different starting concentration of glycerol are likewise known [Büh2002]. Lower temperatures and higher pressures and longer residence times lead to higher relative selectivities, based on acetaldehyde, the maximum conversion of glycerol being relatively low at 31%. Two competing reaction paths are described for the reaction of glycerol. Ionic reaction steps are preferred at higher pressures and/or lower temperatures, whereas free-radical reactions take place at lower pressures and/or higher temperatures. Acetaldehyde can be formed by both routes and is the main product under all conditions. The reaction mechanisms described for the formation of acetaldehyde differ here from the reaction routes assumed to date. The complete reaction model and the kinetic parameters of the reaction of glycerol can, after optimization, be adapted to the measured data obtained.

It is furthermore known that acetaldehyde forms in the homogeneously catalysed dehydration of ethylene glycol in near-critical and supercritical water [Ott2005]. Thus, acetaldehyde can be obtained with a yield of 10% with addition of catalytic amounts of zinc sulphate to a dilute ethylene glycol solution. By using 20 mM sulphuric acid as a catalyst, the yield can be increased to about 80% at 400° C. and 34 MPa and with a residence time of 15 s. Moreover, zinc sulphate catalyses the subsequent reactions of acrolein from the dehydration of glycerol. For an aqueous 1% (g g$^{-1}$) acrolein solution, the conversion is 62% at 360° C. and 34 MPa and with a residence time of 120 s. Liquid reaction products cannot be found. Once again, the corrosiveness of the sulphuric acid under the stated conditions is disadvantageous.

In addition, it is known that acetaldehyde is obtained in the dehydration of very dilute aqueous glycerol solutions without addition or addition of sulphuric acid under the near-critical and supercritical conditions in a batch or flow-tube reactor

[Wat2007]. The maximum yield of acetaldehyde is about 23% for the continuous dehydration of a 0.05 M glycerol solution at 400° C. and 34.5 MPa and with a residence time of 20 s and addition of 5 mM sulphuric acid. The yields without catalyst are significantly lower. The low starting concentrations of glycerol in combination with the use of sulphuric acid as a catalyst are disadvantageous.

DESCRIPTION OF THE INVENTION

The technical problem to be solved consists in reacting the produced acrolein in a second state continuously in high yields without use of sulphuric acid and with short residence times to give acetaldehyde, in order to increase the overall yield of acetaldehyde from glycerol. This problem is solved by the process according to the invention, which is characterized in that acrolein and one or more ammonium salts dissolved in water are reacted continuously under high pressures and at temperatures of 300-400° C.

The process according to the invention preferably takes place in a pH range of 4-8, particularly preferably of 4-6.

It is particularly preferred according to the invention to carry out the reaction in an acidic reaction medium, with the result that the formation of metal hydroxides and/or polymerization reactions of the acrolein can be prevented.

Inorganic ammonium salts, in particular ammonium sulphate, ammonium hydrogen sulphate, ammonium acetate and ammonium dihydrogen phosphate, are particularly preferred.

The use of the ammonium salts leads to the establishment of a pH range in which the retro-aldol reaction of acrolein to give acetaldehyde is favoured. In addition to acetaldehyde, 3-methylpyridine and gaseous products are formed. Formaldehyde, which could be detected qualitatively, also forms as a coproduct. The separation of acetaldehyde from 3-methylpyridine can be effected with very little effort.

The process according to the invention achieves a maximum acetaldehyde yield of 40-62%, based on the starting compounds used.

The process according to the invention can be carried out both directly with the acrolein-containing reaction mixture of the acrolein synthesis step and with acrolein purified beforehand.

Depending on the density of the medium, according to the invention residence times of 5-240 s are preferably set.

According to the invention, the reactions preferably take place at not more than 400° C. and 40 MPa.

The process according to the invention can be carried out in standard high-pressure units. A unit having a flow-tube reactor comprising Inconel625 and a reactor volume of 4-50 ml is preferred here. The starting mixtures are transported via two preheated separate trains with not more than 35 ml min$^{-1}$ into the reactor.

The present invention is explained in more detail by the following, nonlimiting examples.

EXAMPLE 1

Figure 1:
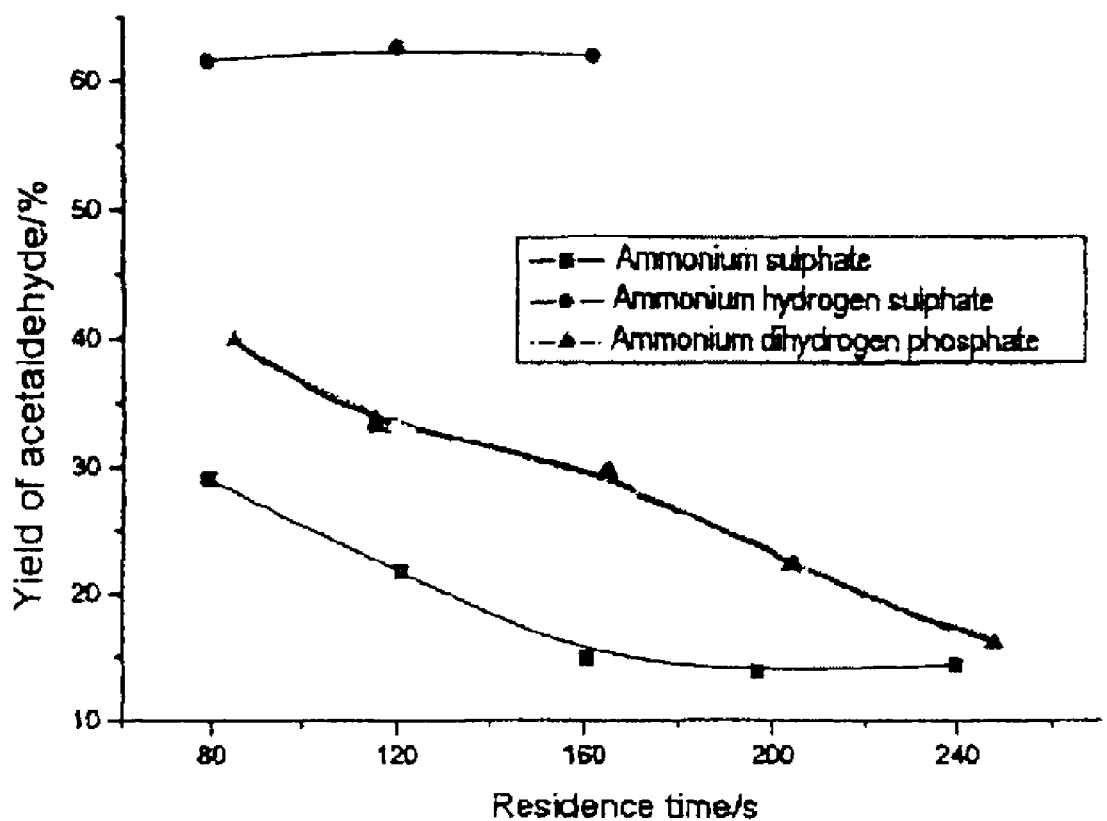
FIG. 1 is a graph which shows yields of acetaldehyde in the continuous reaction of acrolein with ammonium salts in near-critical water at 360° C. and 30 MPa and with different residence times.

An aqueous solution comprising 0.75% (g g$^{-1}$) of acrolein and 1.77% (g g$^{-1}$) of ammonium sulphate or 3.15% (g g$^{-1}$) of ammonium hydrogen sulphate or 3.07% (g g$^{-1}$) of ammonium dihydrogen phosphate, which corresponds to a molar ratio of acrolein to ammonium ions of 1:2, is reacted in a two-train high-pressure unit at 30 MPa. The liquid mixture is first heated to 170° C. in a preheating stage and then mixed with twice the amount of hot water so that, at the reactor entrance of a tubular reactor comprising Inconel625 and having a volume of 49.5 ml, the reaction temperature of 360° C. is established and near-critical water conditions prevail. Depending on the volume flow rate and density of the reaction medium, residence times of 60-240 s are established. The reaction solution is then cooled to room temperature in a heat exchanger and depressurized to atmospheric pressure. In a phase separator, the liquid components are separated from the gaseous ones at 2° C. The liquid phase is collected and the fractions of the detectable components are determined by gas chromatography. For the quantitative determination of the acetaldehyde and of the acrolein, 1-butanol is added to the sample as an internal standard. The acetaldehyde yields determined under the conditions described are shown in FIG. 1. The maximum acetaldehyde yield is 62% at all measured residence times with ammonium hydrogen sulphate.

EXAMPLE 2

Figure 2:
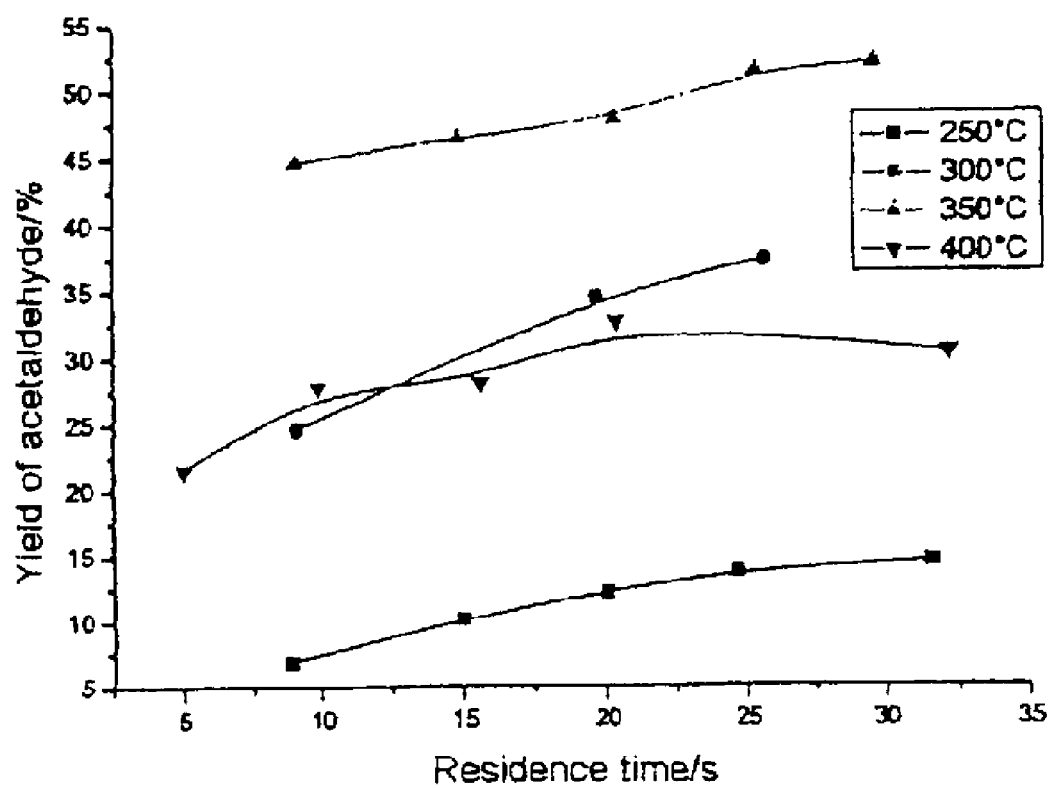
FIG. 2 is a graph which depicts yields of acetaldehyde in the continuous reaction of 0.25% (g g$^{-1}$) with 0.59% (g g$^{-1}$) of ammonium sulphate in near-critical at 30 MPa and with different temperatures and residence times.

The reaction takes place with acrolein and ammonium sulphate in a molar ratio of 1:1. An aqueous solution comprising 0.75% (g g$^{-1}$) of acrolein is first heated to 50° C. in a preheated stage and then mixed with twice the amount of a preheated aqueous solution comprising 0.89% (g g$^{-1}$) of ammonium sulphate, so that the reaction temperature is established at the reactor entrance of a flow-tube reactor (Inconel625; 4.4 ml reactor volume). Depending on the volume flow rate and density of the reaction medium, residence times of 5-35 s are established. The results are shown in FIG. 2. The maximum acetaldehye yield is 52% at a temperature of 350° C. and with a residence time of 30 s.

REFERENCES

[Ant1985] M. J. Antal Jr., W. S. L. Mok, J. C. Roy, A. C. Raissi, D. G. M. Anderson: Pyrolytic sources of hydrocarbons from Biomass, *Journal of Analytical and Applied Pyrolysis*, 1985, 8, 291-303.

[Ant1987] M. J. Antal Jr., A. Britain, C. DeAlmeida, W. S. L. Mok, S. Ramayya: Catalyzed and uncatalyzed conversion of cellulose biopolymer model compounds to chemical feedstocks in supercritical solvents, *Energy from Biomass and Wastes*, 1987, 10, 865-877.

[Büh2002] W. Bühler, E. Dinjus, H. J. Ederer, A. Kruse, C. Mas: Ionic reactions and pyrolysis of glycerol as competing reaction pathways in near- and supercritical water, *Journal of Supercritical Fluids*, 2002, 22, 37-53.

[Eck2007] M. Eckert, G. Fleischmann, R. Jira, H. M. Bolt, K. Golka: Acetaldehyde, Ullmann's Encyclopedia of Industrial Chemistry, 7. Aufl., *Wiley Interscience*, Online Release, 2009.

[Ott2005] L. Ott: Stoffliche Nutzung von Biomasse mit Hilfe von nah-und überkritischem Wasser—homogenkatalysierte Dehydratisierung von Polyolen zu Aldehyden—[Material use of biomass with the aid of near-critical and supercritical water-homogeneously catalysed dehydration of polyols to give aldehydes], Thesis, TU Darmstadt, 2005.

[Ott2006] L. Ott, M. Bicker, H. Vogel: Catalytic dehydration of glycerol in sub- and supercritical water: a new chemical process for acrolein production, *Green Chemistry*, 2006, 8, 214-220.

[Ram1987] S. Ramayya, A. Brittain, C. DeAlmeida, W. S. L. Mok, M. J. Antal Jr.: Acid-catalyzed dehydration of alcohols in supercritical water, *Fuel,* 1987, 66(10), 1364-71.

[Wat2007] M. Watanabe, T. Iida , Y. Aizawa, T. M. Aida, H. Inomata: Acrolein synthesis from glycerol in hot-compressed water, *Bioresource Technology,* 2007, 98, 1285-1290.

The invention claimed is:

1. Process for the selective preparation of acetaldehyde, characterized in that acrolein and one or more ammonium salts dissolved in water are reacted continuously under high pressures and at temperatures of 300-400° C.

2. Process according to claim 1, characterized in that ammonium sulphate, ammonium hydrogen sulphate, ammonium acetate and/or ammonium dihydrogen phosphate are used.

3. Process according to claim 1, characterized in that the acrolein and the ammonium salt are used in a molar ratio of 1:0.125 to 1:2.

4. Process according to claim 1, characterized in that the reaction takes place at pressures of 20-40 MPa.

5. Process according to claim 1, characterized in that the contact or residence time is 5-240 s.

6. Process according to claim 1, the pH of the aqueous solution being in a range of 4-8.

7. Process according to claim 1, the acetaldehyde yield being 40-62%, based on the starting compounds used.

8. Process according to claim 1, formaldehyde forming as a coproduct.

9. Process according to claim 1, the acrolein being obtained from glycerol.

10. Process according to claim 1 characterized in that the contact or residence time is 30-160 s.

* * * * *